(12) United States Patent
Kurosawa et al.

(10) Patent No.: US 7,169,573 B2
(45) Date of Patent: Jan. 30, 2007

(54) METHOD FOR MONITORING COAGULABILITY AND HYPERCOAGULABLE STATES

(75) Inventors: Shinichiro Kurosawa, Edmond, OK (US); Deborah J. Stearns-Kurosawa, Edmond, OK (US)

(73) Assignee: Oklahoma Medical Research Foundation, Oklahoma City, OK (US)

( * ) Notice: Subject to any disclaimer, the term of this patent is extended or adjusted under 35 U.S.C. 154(b) by 650 days.

(21) Appl. No.: 10/028,741

(22) Filed: Dec. 20, 2001

(65) Prior Publication Data

US 2006/0286614 A1 Dec. 21, 2006

Related U.S. Application Data

(60) Provisional application No. 60/270,066, filed on Feb. 20, 2001.

(51) Int. Cl.
  G01N 33/53 (2006.01)
  C07K 14/745 (2006.01)
  C07K 14/705 (2006.01)
  G01N 33/96 (2006.01)

(52) U.S. Cl. .................. 435/7.8; 435/7.92; 435/7.1; 530/350; 530/381; 530/395; 514/802; 514/822

(58) Field of Classification Search .......... 530/381, 530/350, 395; 424/94.67, 94.1, 529, 530; 435/4, 7.8, 7.92; 514/802, 822
See application file for complete search history.

(56) References Cited

U.S. PATENT DOCUMENTS

| 5,804,392 | A | 9/1998 | Esmon et al. |
| 5,935,802 | A | 8/1999 | Lind |
| 5,981,285 | A | 11/1999 | Carroll et al. |
| 6,037,450 | A | 3/2000 | Esmon et al. |

FOREIGN PATENT DOCUMENTS

WO  WO 96/05303  2/1996

OTHER PUBLICATIONS

Esmon et al., Endothelial protein C receptor, Thromb. Haemost. (Aug. 1999) 82(2):251-258.*
Wu et al., Detection of soluble endothelial protein C receptor (sEPCR) in patients with CHD, DM, and SLE, Chung-Hua Hsueh Yeh Hsueh Tsa Chih [Chinese Journal of Hematology] (Sep. 2000) 21(9):472-474.*
Esmon. CT, The endothelial cell protein C receptor, Thromb. Haemost. (May 2000) 83(5):639-643.*
Stearns-Kurosawa et al., Plasma levels of endothelial protein C receptor respond to anticoagulant treatment, Hemost. Thromb. Vasc. Biol. (Jan. 15, 2002) 99(2):526-530.*
Stearns-Kurosawa et al. Bimodal distribution of soluble endothelial protein C receptor levels in healthy populations, J. Thromb. Haemost (Apr. 2003) 1(4):855-856.*
Debeir et al., (1997) Pharmacological characterization of protease-activated receptor (APR-1) in rat astrocytes, Eur. J. Pharm. 323:111-117.*
Breckenridge, "Oral Anticoagulant Drugs: Pharmacokinetic Aspects," *Semin. Hematol.*, 15:19-26, 1978.
Esmon, "Natural Anticoagulants and Their Pathways," in *Handbook of Experimental Pharmacology*, ed: Born et al., Springer-Verlag, New York; pp. 447-476, 1999.
Fukudome and Esmon, "Identification, cloning, and regulation of a novel endothelial cell protein C/activated protein C receptor," *J. Biol. Chem.* 269:26486-26491, 1994.
Fukudome et al., "The endothelial cell protien C receptor. Cell surface expression and direct ligand binding by the soluble receptor," *J Biol Chem.*, 271(29):17491-17498, 1996.
Goldstein et al., "Is Glycohemoglobin Testing Useful in Diabetes Mellitis? Lessons from the Diabetes Control and Complications Trial," *Clin. Chem.*, 40:1637-1640, 1994.
Hrish et al., "Oral Anticoagulants: Mechanisms of Action, Clinical Effectiveness and Optimal Therapeutic Range," *Chest*, 114 Supp. 445S-469S, 1998.
Kurosawa et al., "Identification of Functional Endothelial Protein C Receptor in Plasma," *J. Clin. Invest.*, 100:411-418, 1997.
Kurosawa et al., "Plasma Levels of Endothelial Protein C Receptor are Elevated in Patients with Sepsis and Systemic Lupus Erythmatosus: Lack of Correlation with Thrombomodulin Suggests Different Pathological Processes," *Blood*, 91:725-727, 1998.
O'Reilly, "Vitamin K and the Oral Anticoagulant Drugs," *Annu. Rev. Med.*, 27:245-261, 1976.
Regan et al., "The endothelial cell protein C receptor," *J. Biol. Chem.* 271:17499-17503, 1996.
Riley et al., "Clinical Utilization of the International Normalized Ratio (INR)," *J. Clin. Lab. Anal.*, 14:101-114, 2000.
Stearns-Kurosawa et al., "Plasma levels of endothelial protein C receptor respond to anticoagulant treatment," *Blood*, 99(2):526-530, 2002.
Stearns-Kurosawa et al., "The endothelial cell protein C receptor augments protein C activation by the thrombin-thrombomodulin complex," *Proc. Nat'l Acad. Sci. USA*, 93:10212-10216, 1996.
Sutcliffe et al., "Aspects of Anticoagulant Action: A Review of the Pharmacology, Metabolism and Toxicology of Warfarin and Cogeners," *Rev. Drug Metabol. Drug Interact*, 5:225-272, 1987.
Takahashi et al., "Circulating Thrombomodulin as a Novel Endothelial Cell Marker: Comparison of Its Behavior with von Willebrand Factor and Tissue-Type Plasminogen Activator," *Am. J. Hematol.*, 41:32-39, 1992.
Takano et al., "Plasma Thrombomodulin in Health and Diseases," *Blood*, 76:2024-2029, 1990.
Wada et al., "Plasma Thrombomodulin as a Marker of Vascular Disorders in Thrombotic Thrombocytopenic Purpura and Disseminated Intravascular Coagulation," *Am. J. Hematol.*, 39:20-24, 1992.
Xu et al., "Metalloproteolytic Release of Endothelial Protein C Receptor," *J. Bio. Chem.*, 275:6038-6044, 2000.

(Continued)

*Primary Examiner*—Lorraine Spector
*Assistant Examiner*—Claire M. Kaufman
(74) *Attorney, Agent, or Firm*—Fulbright & Jaworski (57) ABSTRACT

The assay of soluble endothelial protein C receptor (sEPCR) is useful to monitor effective thrombin levels and a hypercoagulable state. An assay for sEPCR is therefore useful to monitor ongoing effectiveness of anticoagulant therapy. A sEPCR ELISA assay is particularly useful for this purpose. A state of hypercoagulability in patients or normal individuals can also be identified by such an assay.

16 Claims, 7 Drawing Sheets

OTHER PUBLICATIONS

Abraham et al., "Efficacy and safety of monoclonal antibody to human tumor necrosis factor alpha in patients with sepsis syndrome: a randomized, controlled, double-blind, multicenter clinical trial," *JAMA*, 273(12):934-941, 1995.

Barthold, "'Muromics': genomics from the perspective of the laboratory mouse," *Comparative Medicine*, 52(3):206-223, 2002.

Coughlin, "Protease-activated receptors in vascular biology," *Thromb. Haemost.*, 86:296-307, 2001.

Deitch, "Animal models of sepsis and shock: a review and lessons learned," *Shock*, 9(1):1-11, 1998.

Fiedler et al., "Monoclonal antibody to tumor necrosis factor-α prevents lethal endotoxin sepsis in adult rhesus monkeys," *J. Lab. Clin. Med.*, 120:574-588, 1992.

Giudici et al., "Antithrombin replacement in patients with sepsis and septic shock," *Haematologica*, 84:452-460, 1999.

Gu et al. "Endotoxin and thrombin elevate rodent endothelial cell protein C receptor mRNA levels and increase receptor shedding in vivo," *Blood*, 95(5):1687-1693, 2000.

Hinshaw et al., "Survival of primates in LD100 septic shock following therapy with antibody to tumor necrosis factor (TNFα)," *Circulatory Shock*, 30:279-292, 1990.

McCloskey et al., "Treatment of septic shock with human monoclonal antibody HA-1A," *Ann. Intern. Med.*, 121:1-5, 1994.

Minnema et al., "Recombinant human antithromin III improves survival and attenuates inflammatory responses in baboons lethally challenged with *Escherichia coli*, " *Blood*, 95(4):1117-1123, 2000.

Moayeri et al., "*Bacillus anthracis* lethal toxin induces TNF-α-independent hypoxia-mediated toxicity in mice," *J. Clin. Invest.*, 112(5):670-682, 2003.

Taylor et al., "Antithrombin-III prevents the lethal effects of *Escherichia coli* infusion in baboons," *Circulatory Shock*, 26:227-235, 1988.

Tracey et al., "Anti-cachectin/TNF monoclonal antibodies prevent septic shock during lethal bacteraemia," *Nature*, 330:662-664, 1987.

Tracey et al., "Cachectin/tumor necrosis factor induces lethal shock and stress hormone responses in the dog," *Surg., Gynec., Obst.*, 164:415-422, 1987.

Vincent et al., "Clinical trials of immunomodulatory therapies in severe sepsis and septic shock," *CID*, 34:1084-1093, 2002.

Zeni et al., "Anti-inflammatory therapies to treat sepsis and septic shock: a reassessment," *Critical Care Medicine*, 25(7):1095-1110, 1997.

* cited by examiner

METHOD FOR MONITORING COAGULABILITY AND HYPERCOAGULABLE STATES

This application claims benefit of priority to U.S. Provisional Application Ser. No. 60/270,066, filed Feb. 20, 2001, the entire content of which is incorporated by reference herein.

BACKGROUND OF THE INVENTION

I. Field of the Invention

The present invention relates to the fields of vascular biology and inflammation. More particularly, it relates to assays to detect soluble endothelial protein C receptor as a measure of thrombin generation.

II. Related Art

In the U.S., more than 55 million people currently suffer from conditions associated with thrombosis. The American Heart Association has estimated that the annual direct expense to the U.S. healthcare system for the treatment of thrombotic disease exceeds $200 billion. On an annual basis worldwide, nearly 2 million patients will undergo either cardiopulmonary bypass surgery or coronary angioplasty to treat such conditions. Thrombosis and associated diseases affect millions of patients and their manifestations are a source of significant morbidity and mortality.

Perturbations of hemostasis are central to the pathogenesis of a hypercoagulable state and may be triggered by multiple, overlapping influences. These include, but are not limited to environmental effects (surgery, diet, smoking, childbirth, trauma), manifestations of a primary disease (heart disease, diabetes, sepsis, hypertension, autoimmune diseases, malignancy) or inheritable defects in the hemostatic factors (protein C, protein S, factor V Leiden, prothrombin, antithrombin III) (Kearon et al., 2000; Carey et al., 1998; Lane et al., 2000). The clinical settings include disseminated intravascular coagulation (DIC), deep vein thrombosis (DVT), or perioperative DVT prevention and heart conditions such as acute myocardial infarction, mechanical prosthetic heart valves, mitral valve prolapse, atrial fibrillation, rheumatic mitral valve disease, and dilated cardiomyopathy. In the U.S. alone, more than 1.5 million patients with atrial fibrillation or mechanical heart valves are currently undergoing preventative oral anticoagulant therapy to help prevent stroke and thrombus formation.

The current therapeutic approach to a patient with thrombotic disease typically starts with an intravenous course of unfractionated heparin or low-molecular weight heparin, followed by a course of oral anticoagulation. Both therapeutic regimes seek to reduce the activity of thrombin, a potent enzyme responsible for activation of the cells and creation of fibrin that form the basis of a clot. In North America, Warfarin (4-hydroxycoumarin) is the most widely used oral anticoagulant, prescribed for preventing and treating venous or arterial thrombosis and embolism.

However, Warfarin is a potentially hazardous drug because the therapeutic window is relatively narrow and the dose-response differs significantly between patients. Warfarin therapy causes major bleeding in about 1–8% of people treated, and intracranial bleeding in about 0.1–0.5% of patients during each year of therapy (van der Meer et al., 1993; Connegieter et al., 1995; Levine et al., NEED YEAR). Patients with transient ischemic attack or minor stroke appear to be particularly at risk for bleeding from Warfarin therapy (Laupacis et al., 1994; *Ann. Nuerol.*, 1997; *N.E. Jour. Med.*, 1995). A small population of patients (0.01–0.1%) may exhibit Warfarin-induced skin necrosis, due to thrombosis of veins and capillaries of the subcutaneous fat (Chan et al., 2000). This can be associated with deficiencies of anti-coagulant proteins, or with unbalanced hemostatic control due to the rapid Warfarin-induced loss of the anticoagulants protein S and/or protein C (hours) compared with the procoagulant protein prothrombin (days). Thus, continual monitoring of coagulation status is required.

Direct measurement of thrombin is virtually impossible, due to its 30-second half-life in the circulation. While this appears to be a short time, thrombin is an extraordinarily potent enzyme and 30 seconds is more than enough time for it to act on its protein substrates and cellular receptors. Thus, the challenge to coagulation test designers is to create an assay that reflects thrombin levels without interference from other proteins or in vitro parameters, an assay that is reproducible and can be standardized, and ideally an assay that reports a history of thrombin levels. This latter challenge is equivalent to that provided by hemoglobin Alc (glycohemoglobin) levels in diabetic patients. Patient compliance and therapeutic efficacy is measured in these patients by the glycosylation levels of their hemoglobin Alc, in essence a mirror of their plasma glucose levels over a 2–4 month period (Goldstein et al., 1994). For patients on oral anticoagulant therapy, none of these challenge parameters are met by the currently available anticoagulation tests, and improved methods are needed.

SUMMARY OF THE INVENTION

Thus, in accordance with the present invention, there is provided a method for monitoring effective thrombin levels in patients undergoing anticoagulant therapy comprising measuring circulating levels of soluble endothelial protein C receptor (sEPCR), wherein lowered sEPCR levels relate to lowered effective thrombin activity. The anticoagulant therapy may involve a vitamin K antagonist, may involve at least one of Warfarin, Coumadine, Previscan, Sintrom, heparin, low molecular weight heparin, pentasaccharides, hirudin, hirudin analogs, coagulation factor inhibitors, protein C pathway components, tissue factor pathway inhibitors, anti-platelet compounds or fibrinolytic pathway components. The sEPCR may be measured by an immunoassay, for example, by ELISA. The circulating sEPCR levels may be determined from a sample such as a blood product (serum, plasma), cerebrospinal fluid or urine.

In another embodiment, there is provided a method for monitoring effectiveness of anticoagulant therapy comprising measuring circulating sEPCR levels, wherein decreases in sEPCR indicate that the anticoagulant therapy is effective. The anticoagulant therapy may involve a vitamin K antagonist, may involve at least one of Warfarin, Coumadine, Previscan, Sintrom, heparin, low molecular weight heparin, pentasaccharides, hirudin, hirudin analogs, coagulation factor inhibitors, protein C pathway components, tissue factor pathway inhibitors, anti-platelet compounds or fibrinolytic pathway components. The sEPCR may be measured by an immunoassay, for example, by ELISA. The circulating sEPCR levels may be determined from a sample such as a blood product (serum, plasma), cerebrospinal fluid or urine.

In yet another embodiment, there is provided a method for identifying individuals in a hypercoagulable state comprising measuring circulating levels of soluble endothelial protein C receptor (sEPCR), wherein elevated sEPCR levels relate to hypercoagulabiity. The sEPCR may be measured by an immunoassay, for example, by ELISA. The circulating sEPCR levels may be determined from a sample such as a blood product (serum, plasma), cerebrospinal fluid or urine.

In still yet another embodiment, there is provided a method for identifying a patient at risk of developing a hypercoagulability state comprising measuring circulating levels of soluble endothelial protein C receptor (sEPCR), wherein elevated sEPCR levels relate to an increased risk of hypercoagulability. The sEPCR is measured by an immunoassay, for example, by ELISA. The patient may have a condition frequently associated with hypercoagulability, such as cancer, sepsis, diabetes, heart diseases, atherosclerosis or autoimmune disease. The sEPCR may be measured by an immunoassay, for example, by ELISA. The circulating sEPCR levels may be determined from a sample such as a blood product (serum, plasma), cerebrospinal fluid or urine.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

In the U.S., more than 55 million people currently suffer from conditions associated with thrombosis. Many of these patients require administration of anticoagulants. Though there are excellent drugs that permit even chronic anticoagulant therapy, these drugs do have adverse effects, such as excess bleeding. Because the therapeutic window for these drugs is both narrow and variable, constant assessment of coagulation status is required.

The key component in the coagulation pathway is thrombin, which is the final enzyme product of the coagulation cascade and is necessary to form fibrin and to activate platelets, both of which are essential components of a clot. Since thrombin itself is virtually impossible to measure, use of surrogate markers is necessary. Currently, there are four tests used clinically to monitor thrombin generation: (a) prothrombin (PT) fragment 1+2 (F1+2); (b) fibrinopeptide A (FpA); (c) thrombin/antithrombin complexes (TAT); and (d) soluble fibrin monomer (SFM). Prothrombin fragment 1+2 is generated when prothrombin is converted to thrombin by factor Xa in the prothrombin complex. It is a peptide released into the circulation with a half-life of about 90 min. Therefore, F1+2 levels will reflect only acute thrombin generation.

Fibrinopeptide A (FpA) is released from fibrinogen by direct thrombin proteolysis. The peptide circulates in the blood and can be detected using a sensitive ELISA. The major drawback of FpA levels is they are very sensitive to in vitro generation of thrombin by phlebotomy techniques and blood handling routines. Some manufacturers have stopped making the ELISA kits and few hematology and coagulation reference laboratories offer the test.

Antithrombin (AT) is the primary inhibitor of thrombin and complexes with thrombin (TAT) to remove it from the circulation. TAT levels can be measured by ELISA. TAT levels also reflect acute generation of thrombin because the complexes are cleared by receptor-mediated mechanism in the liver, limiting evaluation of long-term thrombin levels. Importantly, both F1+2 and TAT levels will reflect both in vivo and artifactual in vitro thrombin generation. Thrombin can be generated in vitro, most commonly by phlebotomy procedures, artificially elevating F1+2 and TAT levels.

Soluble fibrin monomers (SFM) are generated when thrombin cleaves fibrinopeptides A and B from fibrinogen, and the fibrin monomers non-covalently interact with excess fibrinogen. Thrombin then generates factor XIIIa to cross-link the SFM into a local clot or systemic deposition on vascular walls. Thus, increased SFM is more an indication that the normal removal of thrombin is saturated or no longer working properly.

The prothrombin time (PT) assay is a routine is a routine screening method to evaluate the capacity to make a clot. Its usefulness is to detect defects in the overall pathway members. However, the PT assay is more sensitive to agents or events that result in prolongation of the clotting times. There is good correlation between prolonged PT times and bleeding episodes in patients undergoing anticoagulant therapy. However, it is difficult to detect under-dosing of anticoagulant therapy as judged by PT and INR values. Chronic under-treatment maintains a hypercoagulable state, so the patients unknowingly remain at risk for thrombotic events. sEPCR levels will provide a more reliable marker of thrombin activity and report under-dosing of anticoagulant therapy, as well as response to a particular anticoagulant drug.

Thus, the current available tests are subject to interference from in vitro thrombin generation. Furthermore, for relatively stabilized patients on oral anticoagulant therapy who require weekly or monthly monitoring, such tests will report their coagulation status only at the moment of phlebotomy.

The results will not reflect their thrombin levels generated over several days and will not reflect their risk of a possible thrombotic event.

I. THE PRESENT INVENTION

The present inventors have identified a new and improved method for measuring coagulation status. They have determined there is a direct relationship between plasma levels of soluble endothelial protein C receptor (sEPCR) and thrombin generation. Assays for measuring sEPCR have been described previously in U.S. Pat. No. 5,804,392, and may be employed in a variety of distinct embodiments, as discussed below.

First, the present invention involves a method for indirectly monitoring thrombin levels, and hence coagulability, in patients undergoing intravenous or oral anticoagulant therapy, such as treatment with heparin, low-molecular weight heparin, Warfarin, Coumadine, Previscan, Sintrom, inhibitors of coagulation factors or anti-platelet compounds. This method generally comprises measuring levels of soluble endothelial protein C receptor (sEPCR) in patient plasma samples. sEPCR levels relate to thrombin-induced up-regulation of protease activity that results in release of sEPCR. This regulated sEPCR release occurs over a longer time period relative to thrombin generation itself, thus providing a marker for long-term thrombin activity and a hypercoagulable state in patients and in asymptomatic individuals. Available ELISA assays with monoclonal or polyclonal antibodies to sEPCR permit measuring plasma sEPCR levels. Thus, the effectiveness of anticoagulant therapy may be monitored in patients, with particular emphasis on reporting under-dosing and response to therapy.

In addition, the data described herein suggest that sEPCR levels may indicate pathologic hypercoagulability, or elevated risk thereof. Thus, using essentially the same assays for monitoring anticoagulant therapy, the present inventors propose to use sEPCR levels to diagnose or assess risk of hypercoagulable states, for example, those induced by cancer, sepsis, diabetes, heart diseases, atherosclerosis or autoimmune disease. These and other embodiments are described in greater detail below.

II. ANTI-COAGULATION THERAPY AND MONITORING OF COAGULATION STATUS

The basic premise of oral anticoagulant therapy is that it will ultimately reduce thrombin formation by interfering with the vitamin K-dependent coagulation factors required for activation of prothrombin. Thrombin is the final enzyme product of the coagulation cascade and is necessary to form fibrin and to activate platelets, both of which are essential components of a clot. However, thrombin also is necessary for the anticoagulant regulatory system to function properly. The protein C anticoagulant system is a primary regulator of coagulation and thrombin formation (Esmon, 1999). The activated protein C generated by this pathway inactivates critical coagulation factors required for thrombin formation.

An endothelial protein C receptor (EPCR) was recently identified (Fukudome et al., 1994) and shown to facilitate this protein C activation by the thrombin/thrombomodulin system (Stearns-Kurosawa et al, 1996). Soluble EPCR (sEPCR) is found in plasma (Kurosawa et al., 1997) and levels are elevated in patients with sepsis or systemic lupus erythematosus (Kurosawa et al., 1998). The soluble EPCR levels did not correlate with levels of soluble thrombomodulin. Soluble thrombomodulin is generated by neutrophil elastase proteolysis and is an accepted marker of endothelial injury (Takahashi et al., 1992; Takano et al., 1990; Wada et al., 2000). However, sEPCR is generated by different pathways. A recent study demonstrated that sEPCR is generated from its membrane-bound parent by metalloproteinase activity, and this activity is inducible by thrombin and inflammatory mediators (Xu et al., 2000). Thus, in terms of hemostasis, control of thrombin generation is important, but elimination of it entirely may be equally detrimental.

The current therapeutic approach to a patient with thrombotic disease typically starts with an intravenous course of unfractionated heparin or low-molecular weight heparin, followed by a course of oral anticoagulation. Both therapeutic regimes seek to reduce the activity of thrombin, a potent enzyme responsible for activation of the cells and creation of fibrin that form the basis of a clot. In North America, Warfarin (4-hydroxycoumarin) is the most widely used oral anticoagulant, prescribed for preventing and treating venous or arterial thrombosis and embolism. Warfarin and similar coumarin derivatives are vitamin K antagonists that impair the formation and/or action of coagulant proteins (prothrombin, factors VII, IX, X) and anticoagulant proteins (protein C, protein S) (Hrish et al., 1998; Breckenridge, 1978; O'Reilly, 1976; Sutcliffe et al., 1987). Warfarin's onset of 2–7 days and duration of action are predictable and it has excellent bioavailability. Warfarin is rapidly absorbed from the GI tract, reaches maximal blood levels in healthy volunteers in 90 min, and has a half-life of 36–42 hr. Other anticoagulants include heparin, low-molecular weight heparin, pentasaccharides, Previscan, Sintrom, inhibitors of coagulation factors or anti-platelet compounds.

During anticoagulant therapy, the patient coagulation status is monitored using the APTT (activated partial thromboplastin time) and/or the PT (prothrombin time) clotting assays. The APTT assay tests the integrity of the intrinsic and final common pathways of coagulation, so it is sensitive to decreases in the clotting factors or the presence of coagulation factor inhibitors. The PT assay is a useful measure of the extrinsic or initiator pathway of coagulation and, thus, is dependent of the level of factor VII and the common pathway factors II, V, X and fibrinogen. The PT assay is used as a screening test to monitor anticoagulation therapy with Warfarin. Monitoring patient coagulation status is extremely important because the anticoagulant therapeutic regimes may have significant complications, including bleeding episodes.

Close monitoring of patients on oral anticoagulant therapy is required and most patients have daily PT tests until a therapeutic range is achieved, followed by 3 times/week for 7–14 days, then weekly until demonstrated stability permits monthly monitoring. However, standardization of clinical PT results between laboratories has been extremely difficult because the thromboplastin reagent used in the assay exhibits wide variability between manufacturers, depending on the tissue of origin and method of preparation. These sources of variability have made standardization of PT reporting difficult and exposed patients to erratic dosing.

Based on WHO recommendations, the International Normalization Ratio (INR) was adopted in the early 1980s to address this standardization problem. The INR is a calculated value based on the patient's measured PT time and an International Sensitivity Index (ISI) determined by comparison of a commercial thromboplastin with a standard reagent. In the early 1990s, the INR concept was introduced into the U.S. medical community. For most therapeutic anticoagulant applications, an INR value in the range of 2.0 to 3.0 is recommended. Most laboratories now use the INR format worldwide. However, there is general agreement that use of the INR has not eliminated the variability problems (Riley et al., 2000), in part because the manufacturer-assigned ISI values for each thromboplastin lot vary according to the instrument that is used. This remains a significant problem since there are about 270 different reagent-instrument combinations.

III. sEPCR

EPCR is an endothelial cell receptor with significant homology to the CD1/MHC class 1 family (Fukudome and Esmon, 1994; Fukudome et al., 1996; Regan et al., 1996). The cloning and biological role of the endothelial cell receptor for protein C was described in PCT/US95/09636. The protein was predicted to consist of 238 amino acids, which includes a 15 amino acid signal sequence at the N-terminus, and a 23 amino acid transmembrane region which characterizes the receptor as a type 1 transmembrane protein. EPCR binds both protein C and APC with similar affinity (Fukudome et al., 1996) in the presence of calcium, and facilitates protein C activation by presenting the protein C substrate to the thrombin-thrombomodulin activation complex on cell surfaces (Steams-Kurosawa et al., 1996). Recombinant soluble EPCR (rsEPCR), truncated just before the transmembrane domain, binds both protein C and APC with an affinity similar to that observed for intact cell-surface expressed EPCR (Fukudome et al., 1996).

IV. IMMUNOASSAYS

It will be understood that polyclonal or monoclonal antibodies specific for the sEPCR will have utilities in several applications. These include the production of diagnostic kits and in methods of detecting sEPCR. Thus, the invention provides antibodies that bind immunologically to sEPCR. Means for preparing and characterizing antibodies are well known in the art (See, e.g., Antibodies: A Laboratory Manual, Cold Spring Harbor Laboratory, 1988; incorporated herein by reference). Antibodies to sEPCR have already been generated using such standard techniques and are described in U.S. Pat. No. 5,804,392.

A. Polyclonal Antisera

Polyclonal antisera is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccininide ester, carbodiimyde and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization.

A second, booster injection, also may be given. The process of boosting and titering is repeated until a suitable titer is achieved. When a desired level of immunogenicity is obtained, the immunized animal can be bled and the serum isolated and stored, or the animal can be used to generate mAbs (below).

For production of rabbit polyclonal antibodies, the animal can be bled through an ear vein or alternatively by cardiac puncture. The procured blood is allowed to coagulate and then centrifuged to separate serum components from whole cells and blood clots. The serum may be used as is for various applications or else the desired antibody fraction may be purified by well-known methods, such as affinity chromatography using another antibody or a peptide bound to a solid matrix or protein A followed by antigen (peptide) affinity column for purification.

B. Monoclonal Antibodies mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified sEPCR protein, polypeptide or peptide. The immunizing composition is administered in a manner effective to stimulate antibody producing cells.

The methods for generating monoclonal antibodies (MAbs) generally begin along the same lines as those for preparing polyclonal antibodies. Rodents such as mice and rats are preferred animals, however, the use of rabbit, sheep, goat, monkey cells also is possible. The use of rats may provide certain advantages (Goding, 1986, pp. 60–61), but mice are preferred, with the BALB/c mouse being most preferred as this is most routinely used and generally gives a higher percentage of stable fusions.

The animals are injected with antigen, generally as described above. The antigen may be coupled to carrier molecules such as keyhole limpet hemocyanin if necessary. The antigen would typically be mixed with adjuvant, such as Freund's complete or incomplete adjuvant. Booster injections with the same antigen would occur at approximately two-week intervals.

Following immunization, somatic cells with the potential for producing antibodies, specifically B lymphocytes (B cells), are selected for use in the MAb generating protocol. These cells may be obtained from biopsied spleens or lymph nodes. Spleen cells and lymph node cells are preferred, the former because they are a rich source of antibody-producing cells that are in the dividing plasmablast stage.

Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984; each incorporated herein by reference). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag-4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding pp. 71–74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like. The selected hybridomas would then be serially diluted and cloned into individual antibody-producing cell lines, which clones can then be propagated indefinitely to provide mAbs. The cell lines may be exploited for mAb production in two basic ways.

A sample of the hybridoma can be injected (often into the peritoneal cavity) into a histocompatible animal of the type that was used to provide the somatic and myeloma cells for the original fusion (e.g., a syngeneic mouse). Optionally, the animals are primed with a hydrocarbon, especially oils such as pristane (tetramethylpentadecane) prior to injection. The injected animal develops tumors secreting the specific monoclonal antibody produced by the fused cell hybrid. The body fluids of the animal, such as serum or ascites fluid, can then be tapped to provide mAbs in high concentration.

The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography. Fragments of the monoclonal antibodies of the invention can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present invention can be synthesized using an automated peptide synthesizer.

It also is contemplated that a molecular cloning approach may be used to generate monoclonals. For this, combinatorial immunoglobulin phagemid libraries are prepared from RNA isolated from the spleen of the immunized animal, and phagemids expressing appropriate antibodies are selected by panning using cells expressing the antigen and control cells e.g., normal-versus-tumor cells. The advantages of this approach over conventional hybridoma techniques are that approximately $10^4$ times as many antibodies can be produced and screened in a single round, and that new specificities are generated by H and L chain combination which further increases the chance of finding appropriate antibodies.

C. Immunoassays

In still further embodiments, the present invention thus concerns immunodetection methods for binding, quantifying or otherwise generally detecting sEPCR. The steps of various useful immunodetection methods have been described in the scientific literature, such as, e.g., Nakamura et al. (1987; incorporated herein by reference). Immunoassays, in their most simple and direct sense, are binding assays. Certain preferred immunoassays are the various types of enzyme linked immunosorbent assays (ELISAs), radioimmunoassays (RIA) and immunobead capture assay. However, it will be readily appreciated that detection is not limited to such techniques, and Western blotting, dot blotting, FACS analyses, and the like also may be used in connection with the present invention.

In general, immunobinding methods include obtaining a sample suspected of containing a protein, peptide or antibody, and contacting the sample with an antibody or protein or peptide in accordance with the present invention, as the case may be, under conditions effective to allow the formation of immunocomplexes.

The immunobinding methods of this invention include methods for detecting or quantifying the amount of a reactive component in a sample, which methods require the detection or quantitation of any immune complexes formed during the binding process. Here, one would obtain a sample suspected of containing sEPCR, and contact the sample with an antibody, and then detect or quantify the amount of immune complexes formed under the specific conditions.

Contacting the chosen biological sample with the antibody or antisera under conditions effective and for a period of time sufficient to allow the formation of immune complexes (primary immune complexes) is generally a matter of simply adding the composition to the sample and incubating the mixture for a period of time long enough for the antibodies to form immune complexes with sEPCR. After this time, the sample-antibody composition will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any radioactive, fluorescent, biological or enzymatic tags or labels of standard use in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference.

In certain embodiments, the first added component that becomes bound within the primary immune complexes may be detected by means of a second binding ligand that has binding affinity for the encoded protein, peptide or corresponding antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the encoded protein, peptide or corresponding antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

Of particular interest in the present invention are enzyme linked immunosorbent assays, known as ELISAs. In one exemplary ELISA, antibodies binding to the encoded proteins of the invention are immobilized onto a selected surface exhibiting protein affinity, such as a well in a polystyrene microtiter plate. Then, a test composition suspected of containing the sEPCR is added to the wells. After binding and washing to remove non-specifically bound immunocomplexes, the bound antigen may be detected.

Detection is generally achieved by the addition of a second antibody specific for the target protein, that is linked to a detectable label. This type of ELISA is a simple "sandwich ELISA." Detection also may be achieved by the addition of a second antibody, followed by the addition of a third antibody that has binding affinity for the second antibody, with the third antibody being linked to a detectable label.

In another exemplary ELISA, the samples suspected of containing the sEPCR are immobilized onto the well surface and then contacted with the antibodies of the invention. After binding and washing to remove non-specifically bound immunecomplexes, the bound antibody is detected. Where the initial antibodies are linked to a detectable label, the immunecomplexes may be detected directly. Again, the immunecomplexes may be detected using a second antibody that has binding affinity for the first antibody, with the second antibody being linked to a detectable label.

Another ELISA in which the sEPCR are immobilized, involves the use of antibody competition in the detection. In this ELISA, labeled antibodies are added to the wells, allowed to bind to the sEPCR and detected by means of their label. The amount of marker antigen in an unknown sample is then determined by mixing the sample with the labeled antibodies before or during incubation with coated wells. The presence of marker antigen in the sample acts to reduce the amount of antibody available for binding to the well and thus reduces the ultimate signal. This is appropriate for detecting antibodies in an unknown sample, where the unlabeled antibodies bind to the antigen-coated wells and also reduces the amount of antigen available to bind the labeled antibodies.

Irrespective of the format employed, ELISAs have certain features in common, such as coating, incubating or binding, washing to remove non-specifically bound species, and detecting the bound immunecomplexes. For example, in coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is more customary to use a secondary or tertiary detection means rather than a direct procedure. Thus, after binding of a protein or antibody to the well, coating with a non-reactive material to reduce background, and washing to remove unbound material, the immobilizing surface is contacted with a control and sample to be tested under conditions effective to allow immunecomplex (antigen/antibody) formation. Detection of the immunecomplex then requires a labeled secondary binding ligand or antibody, or a secondary binding ligand or antibody in conjunction with a labeled tertiary antibody or third binding ligand.

"Under conditions effective to allow immunecomplex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The "suitable" conditions also mean that the incubation is at a temperature and for a period of time sufficient to allow effective binding. Incubation steps are typically from about 1 to 2 to 4 hrs, at temperatures preferably on the order of 25° to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immunecomplexes between the test sample and the originally bound material, and subsequent washing, the occurrence of even minute amounts of immunecomplexes may be determined.

To provide a detecting means, the second or third antibody will have an associated label to allow detection. Preferably, this will be an enzyme that will generate color development upon incubating with an appropriate chromogenic substrate. Thus, for example, one will desire to contact and incubate the first or second immunecomplex with a urease, glucose oxidase, alkaline phosphatase or hydrogen peroxidase-conjugated antibody for a period of time and under conditions that favor the development of further immunecomplex formation (e.g., incubation for 2 hrs at room temperature in a PBS-containing solution such as PBS-Tween).

After incubation with the labeled antibody, and subsequent to washing to remove unbound material, the amount of label is quantified, e.g., by incubation with a chromogenic substrate such as urea and bromocresol purple or 2,2'-azido-di-3-ethyl-benzthiazoline-6-sulfonic acid (ABTS) and $H_2O_2$, in the case of peroxidase as the enzyme label. Quantitation is then achieved by measuring the degree of color generation, e.g., using a visible spectra spectrophotometer.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Results

Figure 1:
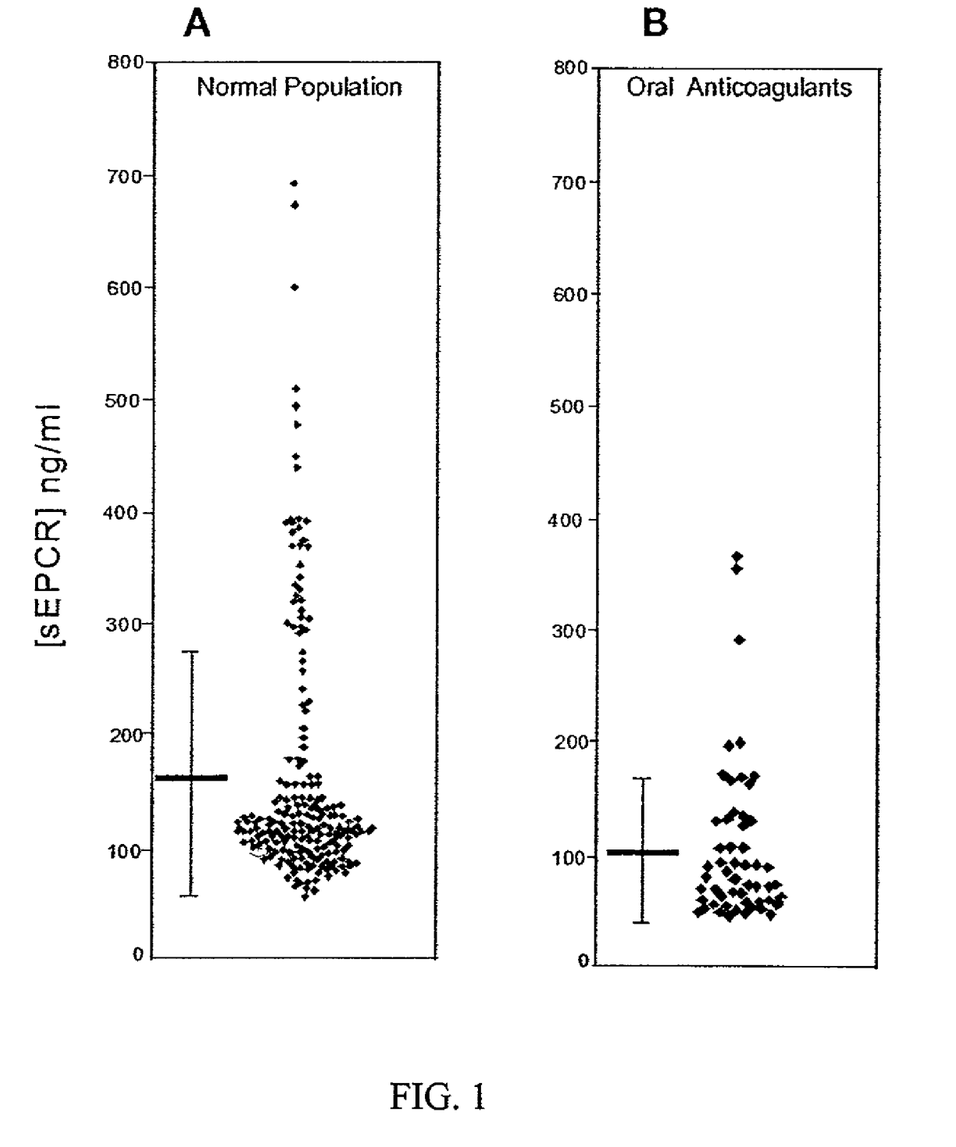
FIG. 1A is a graph showing sEPCR levels in a normal, apparently healthy adult population (n=200; left). The mean and standard deviation is included.
FIG. 1B is a graph showing sEPCR levels in an adult patient population undergoing anticoagulant therapy (n=55). The mean and standard deviation is indicated.
Figure 2:
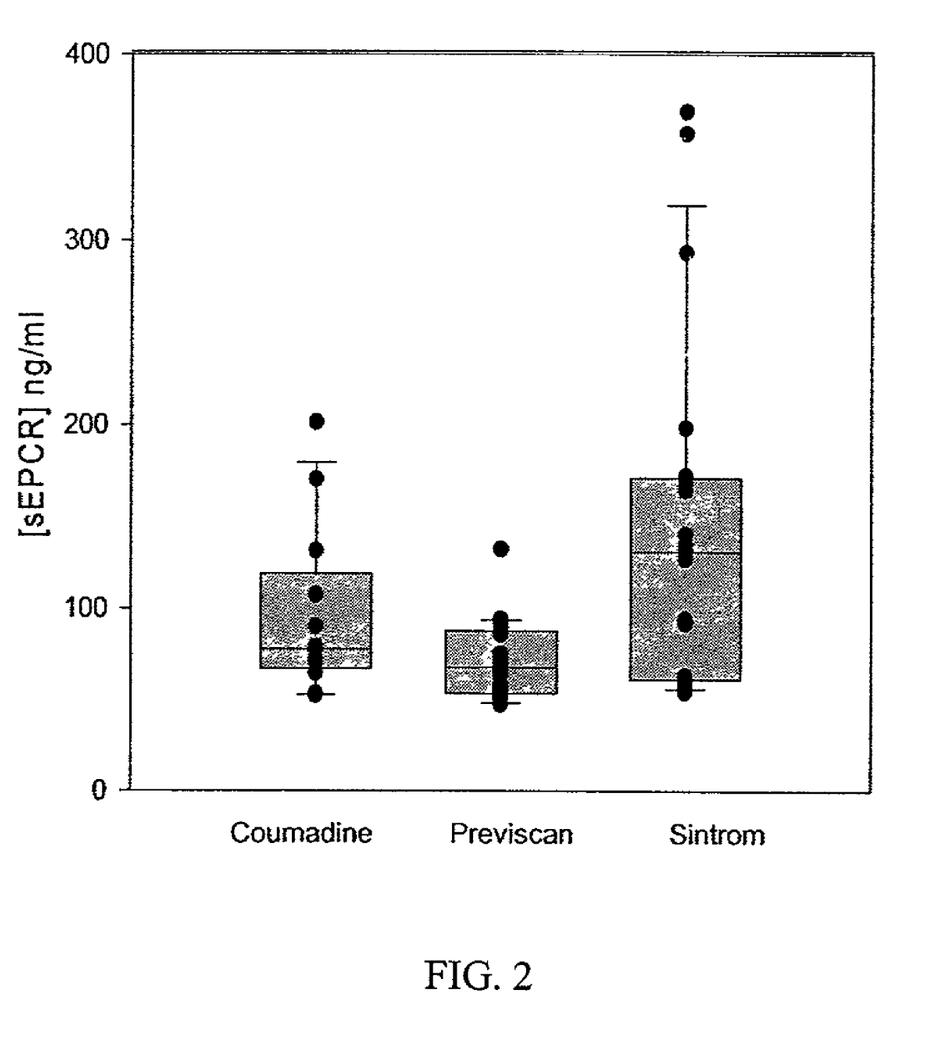
FIG. 2 is a graph showing patient sEPCR levels in a function of the anticoagulation agents Coumadine, Previscan, and Sintrom. The mean and standard deviation is indicated.

Soluble EPCR is generated in vitro by metalloproteinase activity induced by thrombin and some inflammatory mediators (Xu et al., 2000). Thus, the inventors chose to determine whether soluble EPCR levels reflected in vivo thrombin generation. To evaluate this, the soluble EPCR levels were determined in patients on oral anticoagulant therapy and compared with soluble EPCR levels found in a normal, apparently healthy adult population (FIGS. 1A and 1B). These samples were obtained from collaborators in France (Dr. M. Grimeaux, Serbio/Diagnostica Stago). The soluble EPCR levels are assayed using a monoclonal antibody-based enzyme-linked immunosorbent assay (ELISA) (U.S. Pat. No. 5,804,392, incorporated by reference herein). The normal population (see FIG. 1A) had soluble EPCR levels of 165.8+/−115.8 ng/ml. The patients on oral anticoagulant therapy (see FIG. 1B) had significantly lower soluble EPCR levels of 105.3+−70.8 ng/ml (p<0.0001; n=55). Within this patient population, three different oral anticoagulant drugs were used: Coumadine, Previscan, and Sintrom. All three function like Warfarin (coumarin) in that they are vitamin K antagonists. Previscan is a major oral anticoagulant used in France and Germany. Both Coumadine and Previscan have a long half-life (days), whereas that for Sintrom is relatively short (~8.5 hrs). Analysis of the individual data according to the drug used revealed that soluble EPCR levels appeared to be lowest in the patients taking Previscan (FIG. 2). Statistical analysis is difficult, however, because of the different drug clearance rates and it was not known how long the patients had been taking the medications. This is a consideration because the clearance rates of functional coagulation factors from the circulation differ significantly. The half-life for factor VII is only 3–5 hours, whereas that for prothrombin is 60–100 hrs.

Figure 3:
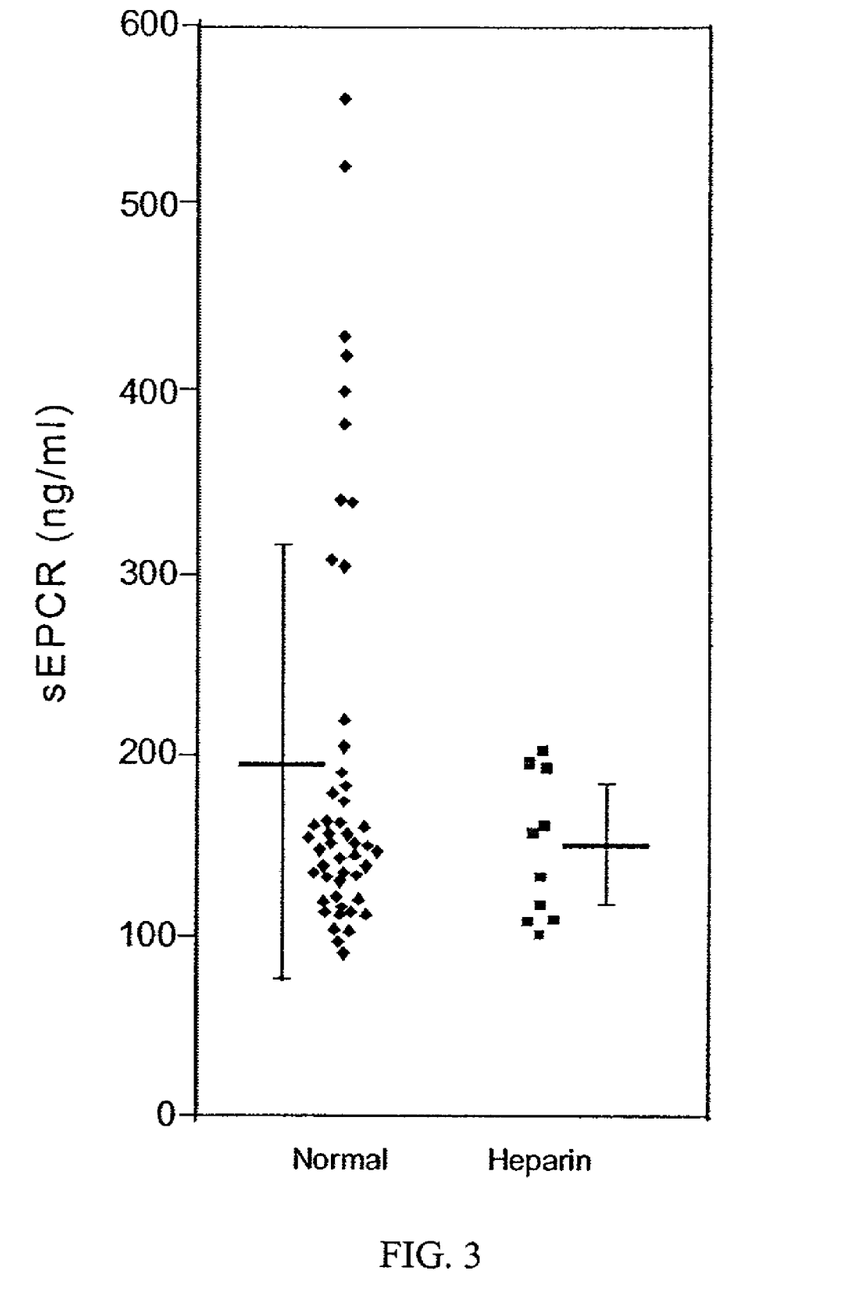
FIG. 3 is a graph showing sEPCR levels in a healthy adult population (n=49; left) and in patients undergoing intravenous anticoagulation therapy with unfractionated heparin (n=10; right). The mean and standard deviation is indicated.

To further evaluate the relationship between plasma sEPCR levels and anticoagulant therapy, samples were obtained from a normal adult population and from patients on intravenous unfractionated heparin therapy (FIG. 3). The data shown in FIGS. 3, 4A, 4B and 5 were obtained from samples contributed by a collaborator in Italy (Dr. Armando D'Angelo, Scientific Institute H. S. Rafeale, Milan, Italy). The normal samples from this Italian population have sEPCR levels of 195.1±114.0 ng/ml (FIG. 3, left; n=49), which does not differ significantly from that observed in samples from France (FIG. 1A). Patients on intravenous heparin therapy have lower sEPCR levels that averaged 147.1±39.3 ng/ml (FIG. 3, right; p<0.09; n=10). While the number of heparin-treated patient samples is small, the reduction of plasma sEPCR levels follows the trend observed above in patients undergoing oral anticoagulant therapy.

Figure 4:
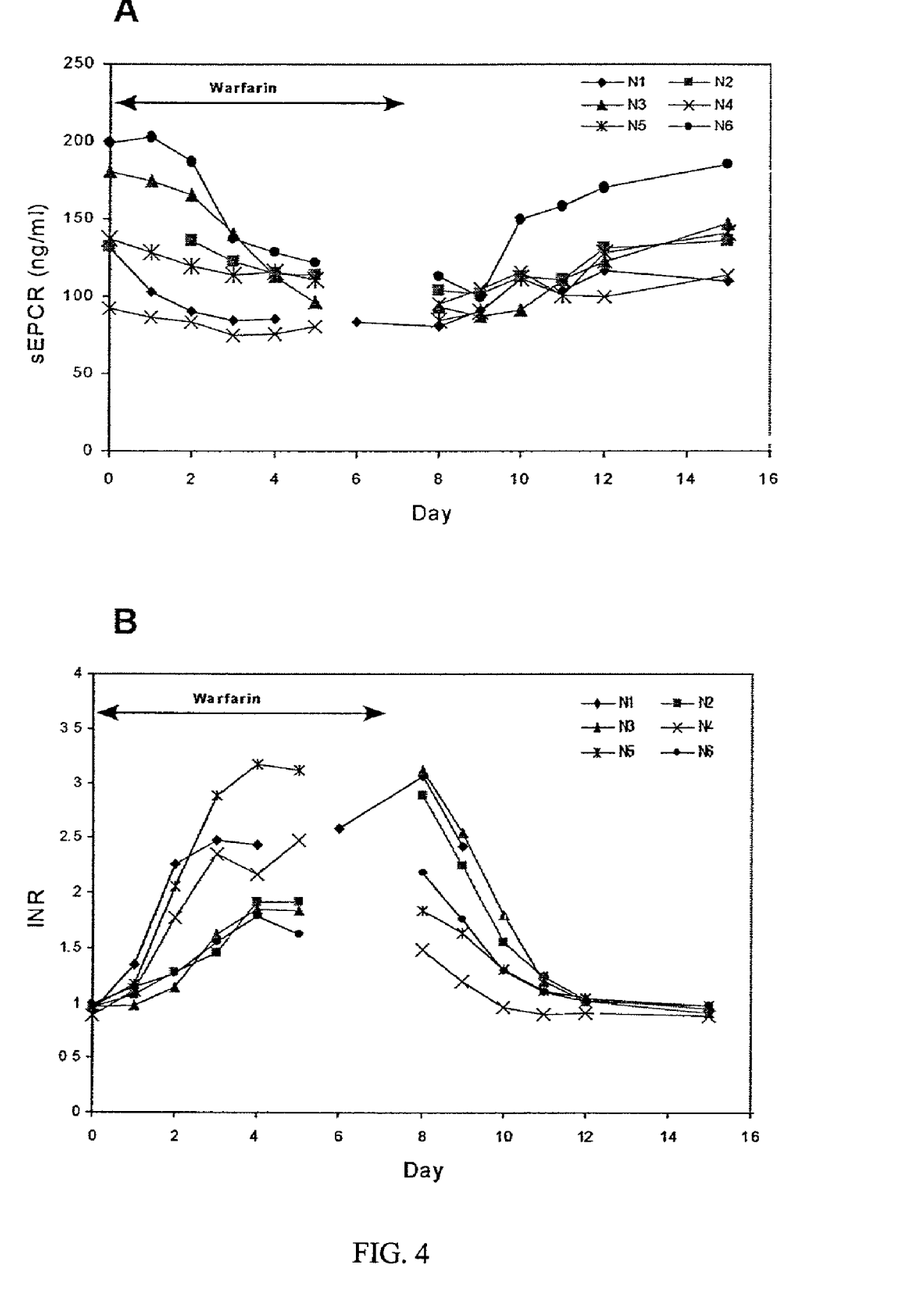
FIG. 4A is a graph showing sEPCR levels in six normal adult subjects administered Warfarin for 7 days, with an additional 7–8 day follow-up period after cessation of the Warfarin.
FIG. 4B is a graph showing the INR values of the six normal adult subjects administered Warfarin for 7 days, with an additional 7–8 day follow-up period after cessation of the Warfarin.

The effect of Warfarin treatment in normal adult subjects on plasma sEPCR levels was studied in 6 adult volunteers with informed consent (FIGS. 4A and 4B). The subjects received Warfarin (oral anticoagulation) for 7 days with an additional follow-up period to day 15. Blood was taken on Day 0 just before starting the Warfarin, then taken each day for evaluation of INR levels. Plasma was stored at −80° C. for determination of sEPCR levels by ELISA. The Warfarin dosage was adjusted as needed for each subject based on their daily INR values. As shown in FIG. 4A, plasma sEPCR levels declined during the Warfarin treatment period. There was a lag time of 24–48 hours before sEPCR levels declined and the extent of decline varied between subjects. Approximately 24–48 hrs after cessation of Warfarin, sEPCR levels began to increase again in all subjects, with most reaching pre-treatment values by day 15. The INR values for these samples were essentially a mirror image of the sEPCR levels (FIG. 4B).

Figure 6:
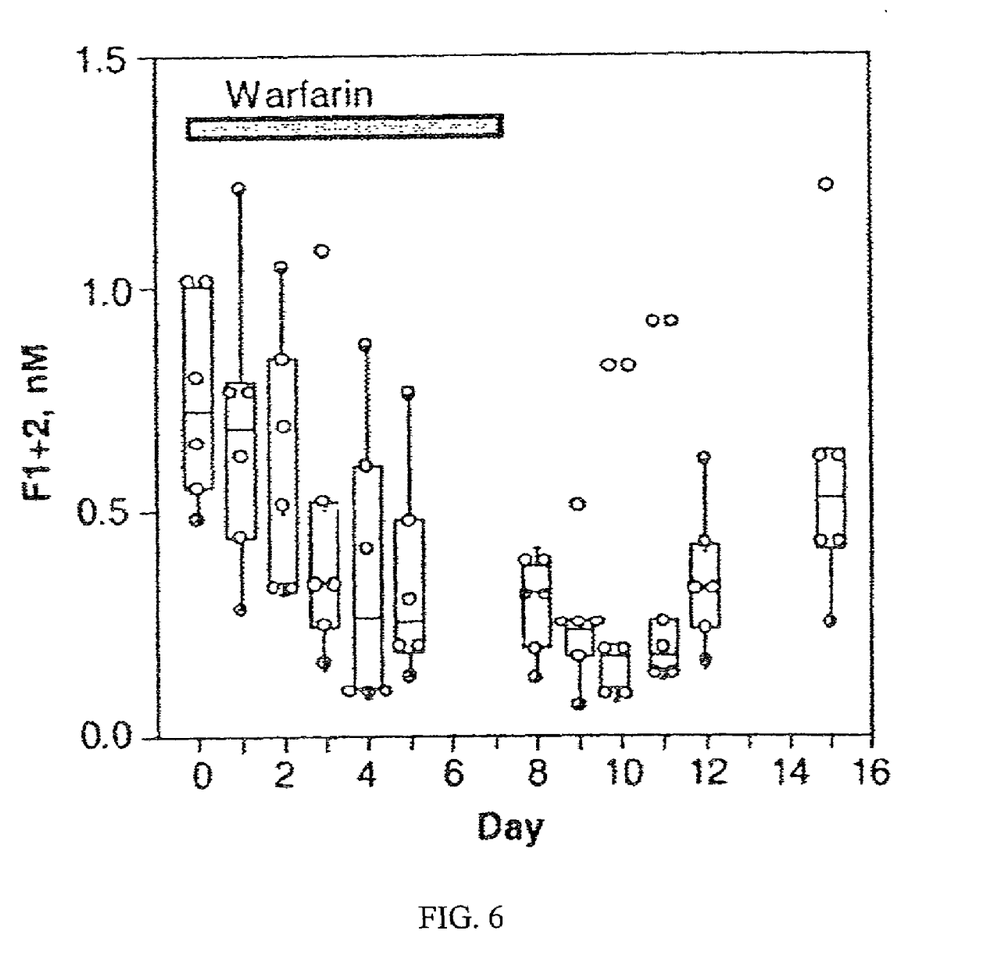
FIG. 6 is a graph showing the F1+2 values of the six normal adult subjects administered Warfarin for 7 days, with an additional 7–8 day follow-up period after cessation of the Warfarin. Levels are shown with median, interquartile ranges, and 95% confiendence intervals for the means.

To confirm that administration of Warfarin is accompanied by a decrease in thrombin production in healthy people, F1+2 levels were monitored (FIG. 6). Levels of F1+2 decreased as a result of the Warfarin administration, with a significant decrease observed on day 5 (to 39% of initial values; P<0.05).

Figure 5:
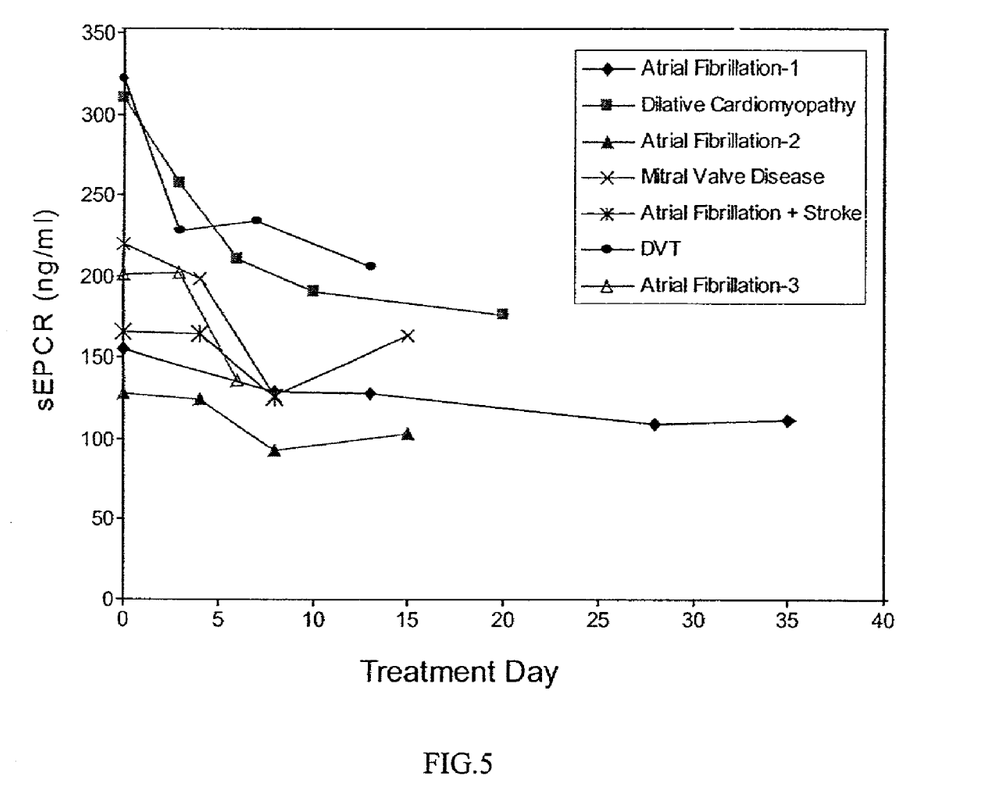
FIG. 5 is a graph showing the sEPCR levels in seven patients before the start of oral anticoagulant therapy and during treatment. The patient diagnoses are indicated. DVT, deep vein thrombosis.
Figure 7:
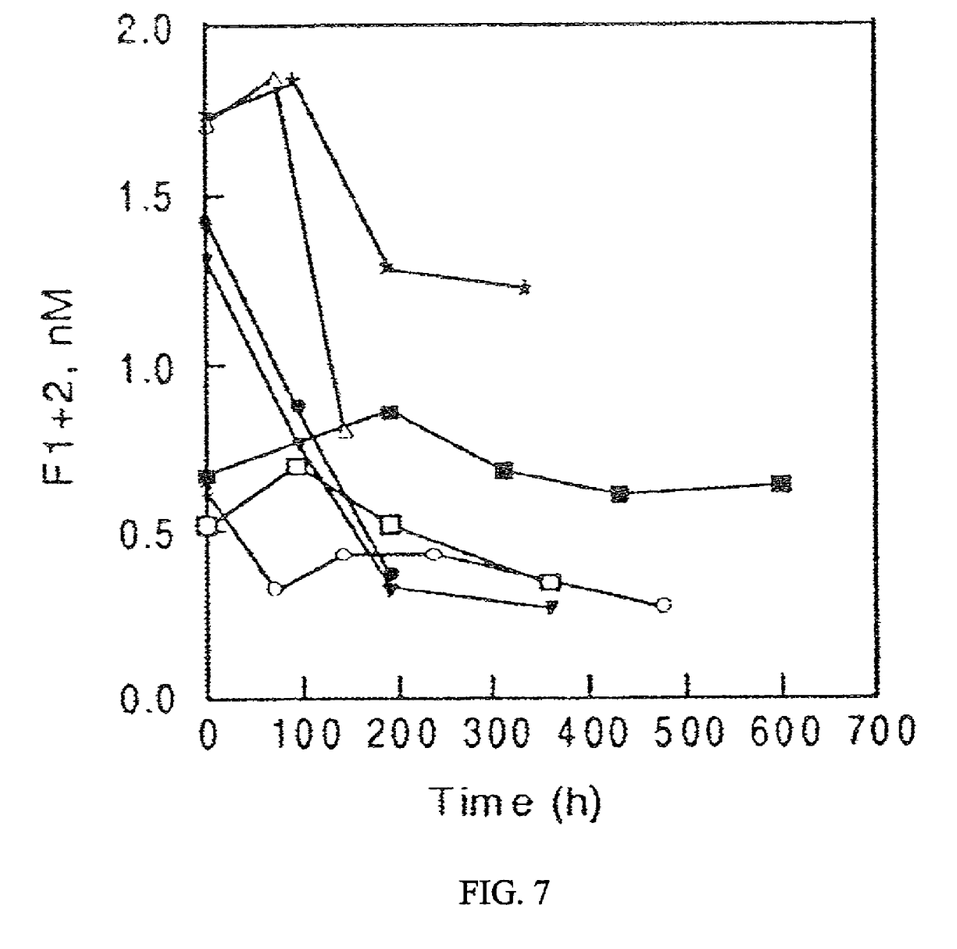
FIG. 7 is a graph showing F1+2 levels in seven patients before the start of oral anticoagulant therapy and during treatment. The patient diagnoses are indicated. Symbols correspond to FIG. 5.

A similar reduction in sEPCR values over time was observed in patients initiating oral anticoagulation therapy (FIG. 5). Blood was taken before the start of anticoagulation and sEPCR levels were determined by ELISA over the course of their therapy. There were 3 patients with atrial fibrillation and one patient each with dilative cardiomyopathy, mitral valve disease, atrial fibrillation+stroke, and deep vein thrombosis (DVT). In all patients studied, sEPCR levels declined with time after starting oral anticoagulant therapy. As with the normal subjects, the extent of the decline in sEPCR levels varied. As expected, F1+2 levels declined in most of the patients after initiation of Warfarin therapy, particularly in those with higher F1+2 levels (FIG. 7).

These observations indicate that not only does oral anticoagulant therapy reduce thrombin generation, it also results in decreased soluble EPCR levels. The data further suggests that a patient with a high, or even therapeutic, INR value and a concomitant high sEPCR level may not be adequately controlled in terms of thrombin generation and the disease pathology. This concept is illustrated by the INR and sEPCR data shown in Table 1 of patients undergoing treatment with the oral anticoagulant Sintrom. Two patients have therapeutic INR values (2.0 and 2.6), yet very elevated sEPCR levels (369 and 357 ng/ml). Another two patients have elevated INR levels (3.3 and 3.6), suggesting higher Sintrom dosages or longer treatment times, yet their sEPCR levels remain elevated (198 and 293 ng/ml). Clinicians tend to rely on INR values to evaluate patient coagulation status and the current data suggests that INR values alone may not be sufficient.

TABLE 1

INR AND SEPCR VALUES IN PATIENTS TAKING SINTROM

| Plasma | INR | [sEPCR] ng/ml |
|---|---|---|
| 1210234 | 1.5 | 140 |
| 1209226 | 1.8 | 135 |
| 1211214 | 1.9 | 167 |
| 1211208 | 2.0 | 369 |
| 1012210 | 2.6 | 63 |
| 1029140 | 2.6 | 357 |
| 1223106 | 2.7 | 131 |
| 1228155 | 2.7 | 92 |
| 1221210 | 2.8 | 127 |
| 1208137 | 3.1 | 59 |
| 1223193 | 3.1 | 61 |
| 928201 | 3.3 | 198 |
| 1221235 | 3.3 | 171 |
| 1228246 | 3.4 | 164 |
| 1012192 | 3.5 | 56 |
| 1208103 | 3.6 | 293 |
| 929179 | 4.5 | 172 |
| 1221195 | >5.0 | 56 |
| 928231 | >5.0 | 61 |
| 929212 | >5.0 | 54 |
| 1006257 | >5.0 | 94 |

Related to this is the observation that there are at least two sub-populations within the normal, apparently healthy population in terms of sEPCR levels. In both the French and Italian subjects studied, the vast majority of sEPCR levels fall within the range of ~75–175 ng/ml (see FIGS. 1A, 1B and 3). The remaining sEPCR levels are scattered from 200–700 ng/ml. While the inventors cannot rule out environmental (smoking, diet) or genetic (polymorphisms, gender) factors, the observation that sEPCR levels in normal subjects during Warfarin treatment (FIGS. 4A and 4B) suggests that these asymptomatic individuals with exceedingly high sEPCR levels may be at risk for a thrombotic event. Thus, sEPCR levels also may be a marker for a hypercoagulable state.

Example 2

Discussion

The current understanding of soluble EPCR formation is that thrombin induces metalloproteinase activity, which then proteolyses the membrane-bound EPCR parent to release the soluble receptor. The in vitro time frame of this process is hours (Xu et al., 2000). This compares with only minutes for thrombin-antithrombin (TAT) formation in the absence of heparin, which is accelerated approximately 2300-fold in the presence of heparin (Beller et al, 1979). Thus, the time frame involved for monitoring sEPCR formation is much longer than for thrombin itself. The data shown in FIGS. 4A and 4B indicates the sEPCR levels in normal individuals begin to fall within 24–48 hours after initiation of Warfarin and, conversely, begin to rise 24–48 hours after cessation of Warfarin. In some patients this may be longer, as shown by three of the patients in FIG. 5, whose sEPCR levels dropped only after day 3–4 of treatment. It also follows that thrombin generated in vitro during phlebotomy, a significant problem with other current tests, will have no effect on soluble EPCR levels. Standardization of soluble EPCR levels also will not be a problem, because the ELISA assay uses standardized reagents from one manufacturer.

A potential use of the present invention involving the soluble EPCR assay encompasses monitoring any patient population that receives oral or other anticoagulant therapy. Some current estimates put this group in the region of at least 2–3 million patients per year. In the United States, more than 1.5 million people with atrial fibrillation or mechanical heart valves are currently taking some kind of oral anticoagulant or anti-platelet rugs to help prevent stroke and related cardiovascular problems. Many more anticoagulant therapeutics that target thrombin generation or activity are either in use (heparin, low-molecular weight heparin) or are being tested (anti-platelet compounds, factor Xa inhibitors) in various patient populations. The coagulation status of all these patients must be monitored to prevent under-dosing and clotting, or overdosing and bleeding. The new assay may be of particular use to report under-dosing of anticoagulant therapies, because the most commonly used clotting screening method (prothrombin time, PT) is relatively insensitive to under-dosing. Thus, many patients may be unknowingly at risk for thrombotic events that could be prevented by better monitoring of their anticoagulant therapy and choice of anticoagulant. Conversely, many patients (e.g., myocardial infarction) may not be at risk for additional thrombosis, yet they automatically continue receiving long-term anticoagulant therapy for preventative purposes because there is no marker available. This sEPCR assay may help clinicians select those patients at low risk for thrombosis, thereby preventing unnecessary medication, trouble and expense to the patient.

Additionally, the sEPCR assay may be used to identify or monitor a hypercoagulable state in patients or in a normal population. Hypercoagulation is a significant problem in many patient populations whose primary disease alters the hemostatic balance. These populations include patients with cancer, sepsis, diabetes, atherosclerosis or autoimmune diseases (Carey et al., 1998) in addition to the heritable and acquired coagulation disorders (Kearon et al., 2000; Carey et al., 1998; Lane et al., 2000). The sEPCR assay may also be of value as a marker for a hypercoagulable state in asymptomatic individuals, analogous to the general use of plasma cholesterol and low-high density lipoprotein (LDL, HDL) levels as markers for an atherosclerotic state. The present inventors have repeatedly observed a sub-population of normal individuals who have exceedingly high sEPCR levels. These individuals comprise about 20–25% of an apparently healthy adult population and they may be at an increased risk for a thrombotic event. There may be factors other than thrombin that contribute to sEPCR levels, but the observation that sEPCR levels in normal subjects fall during Warfarin treatment strongly indicates that thrombin activity has a direct influence on plasma sEPCR levels.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods, and in the steps or in the sequence of steps of the method described herein, without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. REFERENCES

The following references, to the extent that they provide exemplary procedural or other details supplementary to those set forth herein, are specifically incorporated herein by reference:

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 5,804,392
"The European Atrial Fibrillation Trial Study Group. Optimal Oral Anticoagulant Therapy in Patients Without Nonrheumatic Atrial Fibrillation and Recent Cerebral Ischemia," *N.E. Jour. Med.*, 333:5–10, 1995.
"The Stroke Prevention in Reversible Ischemia Trial (SPIRIT) Study Group. A Randomized Trial of Anticoagulants Versus Aspirin after Cerebral Ischemia of Presumed Arterial Origin," *Ann. Nuerol.*, 42:857–965, 1997.
Antibodies: A Laboratory Manual, Cold Spring Harbor Laboratory, Cold Spring Harbor Press, Cold Spring Harbor, N.Y., 1988.
Beller et al, "Fractionation of Low Molecular Weight Heparin Species and Their Interaction with Antithrombin," *J. Biol. Chem.*, 254:2902–2913, 1979.
Breckenridge, A. M., "Oral Anticoagulant Drugs: Pharmacokinetic Aspects," *Semin. Hematol.*, 15:19–26, 1978.
Campbell, In: *Monoclonal Antibody Technology, Laboratory Techniques in Biochemistry and Molecular Biology*, Vol. 13, Burden and Von Knippenberg (Eds.), Elseview, Amsterdam, pp. 71–74; 75–83, 1984.
Carey et al., "Disseminated Intravascular Coagulation: Clinical and Laboratory Aspects," *Amer. J. Hematol.*, 59:69–73, 1998.
Chan et al, "Warfarin Induced Skin Necrosis," *Br. J. Surg.*, 87:266–272, 2000.
Connegieter et al., "Optimal Oral Anticoagulant Therapy in Patients with Mechanical Heart Valves," *N.E. Jour. Med.*, 333:11–17, 1995.
Esmon, C. T., "Natural Anticoagulants and Their Pathways," in *Handbook of Experimental Pharmacology*, [ed: Born, G. V. R., Cuatracasas, P., Gaten, D., Herken, H., Starke, K., Taylor, P.], Springer-Verlag, New York; pp. 447–476, 1999.
Fukudome and Esmon, "Identification, cloning, and regulation of a novel endothelial cell protein C/activated protein C receptor," *J. Biol. Chem.* 269:26486–26491, 1994.
Fukudome et al., "Identification, Cloning and Regulation of a Novel Endothelial Cell Protein C/Activated Protein Receptor," *J. Biol. Chem.*, 269:26486–26491, 1994.
Fukudome et al., "The endothelial cell protein C receptor. Cell surface expression and direct ligand binding by the soluble receptor,": *J. Biol. Chem.*, 271(29):17491–17498, 1996.
Gefter et al., "A simple method for polyethylene glycol-promoted hybridization of mouse myeloma cells," *Somatic Cell Genet*, 3(2):231–6, 1977.
Goding, In: *Monoclonal Antibodies: Principles and Practice*, 2d ed., Academic Press, Orlando, Fla., pp. 60–61, and 71–74, 1986.
Goding, In: *Monoclonal Antibodies: Principles and Practice*, 2d ed., Academic Press, Orlando, Fla., pp. 61–66, 1986.
Goldstein et al., "Is Glycohemoglobin Testing Useful in Diabetes Mellitis? Lessons from the Diabetes Control and Complications Trial," *Clin. Chem.*, 40:1637–1640, 1994.
Hrish et al., "Oral Anticoagulants: Mechanisms of Action, Clinical Effectiveness and Optimal Therapeutic Range," *Chest*, 114 Supp. 445S–469S, 1998.
Kearon et al, "Management of Patients with Hereditary Hypercoagulable Disorders," *Annu. Rev. Med.*, 51:169–185, 2000.
Kohler and Milstein, "Continuous cultures of fused cells secreting antibody of predefined specificity," *Nature*, 256 (5517):495–7, 1975.
Kohler and Milstein, "Derivation of specific antibody-producing tissue culture and tumor lines by cell fusion," *Eur J Immunol*, 6(7):511–9, 1976.
Kurosawa et al., "Identification of Functional Endothelial Protein C Receptor in Plasma," *J. Clin. Invest.*, 100: 411–418, 1997.
Kurosawa et al., "Plasma Levels of Endothelial Protein C Receptor are Elevated in Patients with Sepsis and Systemic Lupus Erythmatosus: Lack of Correlation with Thrombomodulin Suggests Different Pathological Processes," *Blood*, 91:725–727, 1998.
Lane et al., "Role of Hemostatic Gene Polymorphisms in Venous and Aretrial Thrombotic Disease," *Blood*, 95:1517–1532, 2000.
Laupacis et al., "Risk Factors for Stroke and Efficacy of Antithrombotic Therapy in Atrial Fibrillation, Analysis of Pooled Data from Five Randomized Controlled Trials," *Arch. Intern. Med.*, 154:1449–1457, 1994.
Levine et al., "Hemmorhagic Complications of Anticoagulant Treatment," *Chest*, 114 Suppl:511S–523S.
Nakamura et al., In: *Handbook of Experimental Immunology* (4th Ed.), Weir, Herzenberg, Blackwell, Herzenberg, (eds). Vol. 1, Chapter 27, Blackwell Scientific Publ., Oxford, 1987.
O'Reilly, R. A., "Vitamin K and the Oral Anticoagulant Drugs," *Annu. Rev. Med.*, 27:245–261, 1976.
PCT/US95/09636
Regan et al., 1996, *J. Biol. Chem.* 271:17499–17503

Riley et al., "Clinical Utilization of the International Normalized Ratio (INR)," *J. Clin. Lab. Anal.,* 14:101–114, 2000.

Stearns-Kurosawa et al., "The endothelial cell protein C receptor augments protein C activation by the thrombin-thrombomodulin complex," *Proc. Nat'l Acad. Sci. USA,* 93:10212–10216, 1996.

Stearns-Kurosawa et al., "The Endothelial Protein C Receptor Augments Protein C Activation by the Thrombin-Thrombomodulin System," *Proc. Natl. Acad. Sci. USA,* 93:10212–10216, 1996.

Sutcliffe et al., "Aspects of Anticoagulant Action: A Review of the Pharmacology, Metabolism and Toxicology of Warfarin and Cogeners," *Rev. Drug Metabol. Drug Interact,* 5:225–272, 1987.

Takahashi et al., "Circulating Thrombomodulin as a Novel Endothelial Cell Marker: Comparison of Its Behavior with von Willebrand Factor and Tissue-Type Plasminogen Activator," *Am. J. Hematol.,* 41:32–39, 1992.

Takano et al., "Plasma Thrombomodulin in Health and Diseases," *Blood,* 76:2024–2029, 1990.

van der Meer et al, "Bleeding Complications in Oral Anticoagulant Therapy: An Analysis of Risk Factors," *Arch. Intern. Med.,* 153:1557–1562, 1993.

Wada et al., "Plasma Thrombomodulin as a Marker of Vascular Disorders in Thrombotic Thrombocytopenic Purpura and Disseminated Intravascular Coagulation," *Am. J. Hematol.,* 39:20–24, 2000.

Xu et al., "Metalloproteolytic Release of Endothelial Protein C Receptor," *J. Bio. Chem.,* 275:6038–6044, 2000.

What is claimed is:

1. A method for monitoring effective thrombin levels in a human patient undergoing anticoagulant therapy comprising measuring circulating levels of soluble endothelial protein C receptor (sEPCR) of said patient, wherein lowered sEPCR levels relate to lowered effective thrombin activity.

2. The method of claim 1, wherein the anticoagulant therapy involves a vitamin K antagonist.

3. The method of claim 1, wherein the anticoagulant therapy involves at least one of Warfarin, Coumadine, Previscan, and Sintrom.

4. The method of claim 1, wherein the anticoagulant therapy involves use of heparin, low molecular weight heparin, pentasaccharides, hirudin, hirudin analogs, coagulation factor inhibitors, protein C pathway components, tissue factor pathway inhibitors, anti-platelet compounds or fibrinolytic pathway components.

5. The method of claim 1, wherein the sEPCR is measured by an immunoassay.

6. The method of claim 5, wherein the sEPCR is measured by ELISA.

7. The method of claim 1, wherein the sEPCR level is determined by measuring sEPCR in a blood product, cerebrospinal fluid or urine.

8. The method of claim 7, wherein the blood product is plasma or serum.

9. A method for monitoring effectiveness of anticoagulant therapy in a human patient comprising measuring circulating sEPCR levels of said patient, wherein decreases in sEPCR indicate that the anticoagulant therapy is effective.

10. The method of claim 9, wherein the anticoagulant therapy involves a vitamin K antagonist.

11. The method of claim 9, wherein the anticoagulant therapy involves at least one of Warfarin, Coumadine, Previscan, and Sintrom.

12. The method of claim 9, wherein the anticoagulant therapy involves use of heparin, low molecular weight heparin, pentasaccharides, hirudin, hirudin analogs, coagulation factor inhibitors, protein C pathway components, tissue factor pathway inhibitors, anti-platelet compounds or fibrinolytic pathway components.

13. The method of claim 9, wherein the sEPCR is measured by an immunoassay.

14. The method of claim 13, wherein the sEPCR is measured by ELISA.

15. The method of claim 9, wherein the sEPCR level is determined by measuring sEPCR in a blood product, cerebrospinal fluid or urine.

16. The method of claim 15, wherein the blood product is plasma or serum.

* * * * *